United States Patent
Johnson et al.

(10) Patent No.: US 10,088,550 B2
(45) Date of Patent: Oct. 2, 2018

(54) SET A GAS DETECTOR'S LOCATION AUTOMATICALLY USING SHORT RANGE RADIO

(71) Applicant: Honeywell International Inc., Morris Plains, NJ (US)

(72) Inventors: Kirk William Johnson, Calgary (CA); Mahdi Javer, Calgary (CA); Stephen Mroszczak, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 267 days.

(21) Appl. No.: 15/045,573

(22) Filed: Feb. 17, 2016

(65) Prior Publication Data

US 2017/0234963 A1 Aug. 17, 2017

(51) Int. Cl.
| | | |
|---|---|---|
| G01S 5/02 | (2010.01) | |
| G01N 33/00 | (2006.01) | |
| G01S 5/00 | (2006.01) | |
| G08B 21/12 | (2006.01) | |
| G06K 19/07 | (2006.01) | |

(52) U.S. Cl.
CPC ........ G01S 5/0294 (2013.01); G01N 33/0009 (2013.01); G01S 5/0063 (2013.01); G06K 19/0717 (2013.01); G08B 21/12 (2013.01)

(58) Field of Classification Search
CPC ................................ G01S 3/02; G01S 5/0252
USPC ........................................................ 342/451
See application file for complete search history.

(56) References Cited

U.S. PATENT DOCUMENTS

| 9,008,831 B1* | 4/2015 | Jacobs | B65G 47/52 |
| | | | 700/213 |
| 2007/0184852 A1* | 8/2007 | Johnson | H04W 64/00 |
| | | | 455/456.1 |
| 2008/0109099 A1* | 5/2008 | Moshier | G06Q 10/06 |
| | | | 700/103 |
| 2008/0224867 A1* | 9/2008 | Rehman | G06Q 10/08 |
| | | | 340/572.1 |

(Continued)

FOREIGN PATENT DOCUMENTS

| EP | 2009574 A1 | 12/2008 |
| WO | 2017142847 A1 | 8/2017 |

OTHER PUBLICATIONS

International Application No. PCT/US2017/017754, International Search Report, dated May 18, 2017, 3 pages.

(Continued)

*Primary Examiner* — Harry K Liu
(74) *Attorney, Agent, or Firm* — Wick Phillips Gould & Martin, LLP

(57) ABSTRACT

Embodiments relate generally to systems and methods for updating the location information for a gas detector device. A gas detector device may comprise a wireless scanner operable to receive information from one or more passive tags. In some cases, the passive tags may comprise location information. When the gas detector scans a passive tag, the location information stored on the gas detector may be updated accordingly. In some cases, the subsequent readings of the gas detector may be associated with the updated location information. In some cases, the passive tags may be located at critical areas within a facility, such as entrances or exits to locations.

19 Claims, 4 Drawing Sheets

(56) References Cited

U.S. PATENT DOCUMENTS

| | | | |
|---|---|---|---|
| 2009/0174547 A1* | 7/2009 | Greene | A62B 99/00 340/539.13 |
| 2011/0037571 A1* | 2/2011 | Johnson, Jr. | G06K 7/0095 340/10.5 |
| 2011/0169607 A1* | 7/2011 | Paulson | G01S 13/825 340/10.1 |
| 2012/0135527 A1* | 5/2012 | Bangera | G08B 21/245 436/3 |
| 2014/0349707 A1 | 11/2014 | Bang | |
| 2014/0361878 A1 | 12/2014 | Qidwai et al. | |
| 2015/0339837 A1* | 11/2015 | Macfarlane | G06T 11/60 345/634 |
| 2016/0039340 A1* | 2/2016 | Schantz | G01S 5/14 340/435 |
| 2016/0110984 A1* | 4/2016 | Seol | H04W 4/008 340/539.13 |
| 2016/0254844 A1* | 9/2016 | Hull | H04B 5/0062 340/6.1 |

OTHER PUBLICATIONS

International Application No. PCT/US2017/017754, Written Opinion of the International Searching Authority, dated May 18, 2017, 6 pages.

* cited by examiner

SET A GAS DETECTOR'S LOCATION AUTOMATICALLY USING SHORT RANGE RADIO

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, workers may carry gas detectors with them as they work, to allow for detection of gas exposure. The gas detector may alert the user if exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1A:
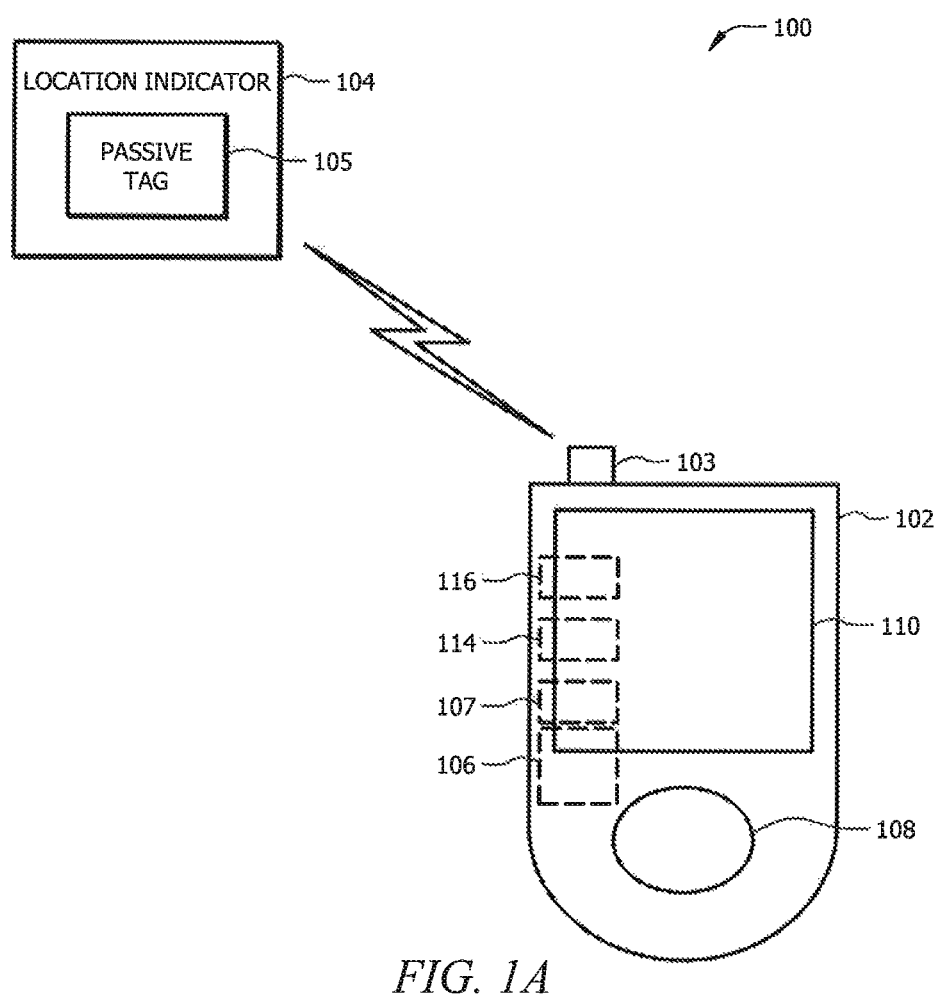
FIGS. 1A-1B illustrate a gas detector device and location indicator according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for updating the location information for a gas detector device. A gas detector device may comprise a wireless scanner operable to receive information from one or more passive tags located throughout a facility. In some cases, the passive tags may comprise location information.

Workers who use gas detectors are sometimes required to indicate their location to the gas detector. For example, the worker may manually enter their current location into the detector. Some detectors may allow a worker to change the location through a series of menus and button presses. Other devices may only have one button and require the user to connect to a computer change the location. This can be incredibly time consuming for the user.

To simplify the process of updating the location of a gas detector, passive short range wireless tags may be installed at key locations within a facility. The passive tag(s) would likely be installed in a poster, making it easy for the user to notice. When the user enters a key location, they may see the poster and scan their detector against the poster to "check in" to that location. The detector may read or scan the passive tag and automatically adjust the location field within its logs.

The passive tags may be designed with a particular location encoded into them. A gas detector may be designed with a short range radio (or wireless scanner) capable of reading the passive tag when it is brought very close to the tag. The gas detector may then automatically read and set the location field in its logs.

Figure 1B:
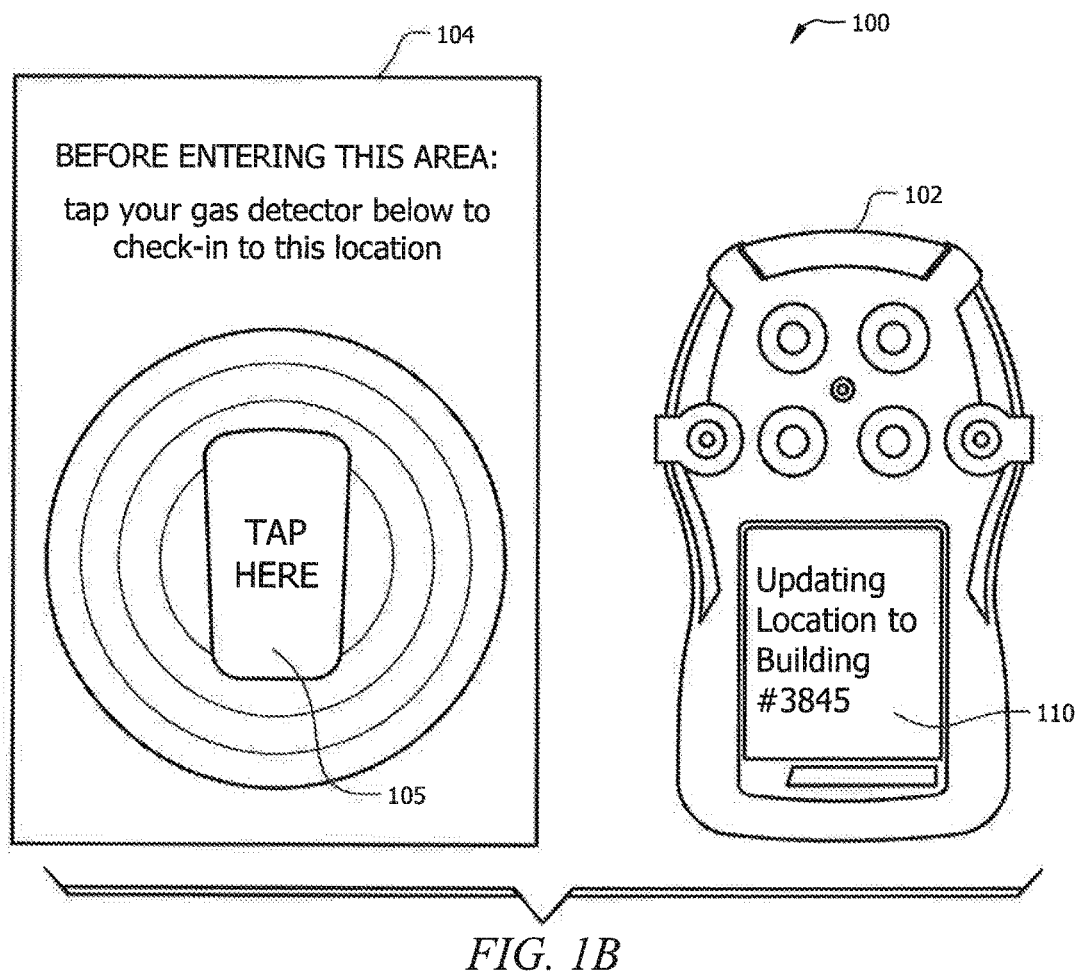

Referring now to FIGS. 1A-1B, a system 100 is shown, including a gas detector device 102, wherein the gas detector device 102 comprises a wireless scanner (or receiver) 106. In some embodiments, the wireless scanner 106 may comprise a short range radio. In some embodiments, the gas detector device 102 may comprise one or more sensors 103, a user interface 110, and one or more buttons 108. The gas detector device 102 may be operable to detect, via the sensors 103, any harmful gases or chemicals in the air near a user who is carrying the gas detector device 102. In some embodiments, the gas detector device 102 may be operable to alert a user based on the input from the one or more sensors 103. In some embodiments, a user may control the gas detector device 102 and input information via the user interface 110 and/or button 108. Additionally, the user may receive information via the user interface 110.

The gas detector device 102 may also comprise a processor 114 and a memory 116. The processor 114 may be operable to receive information from the one or more sensors 103. The processor 114 may also be operable to receive information from the wireless scanner 106. In some embodiments, the gas detector device 102 may also comprise a wireless transmitter 107 operable to communicate wirelessly. In some embodiments, the gas detector device 102 may communicate with a remote monitoring station or other emote device.

The system 100 may also comprise one or more location indicators 104, wherein the location indicators 104 may be placed at critical or important locations, such as at the entrances and/or exits of specific locations. The location indicator 104 may comprise a passive wireless tag 105 operable to communicate information about the location indicator 104 when scanned. In some embodiments, the passive tag 105 may comprise a near-field communication (NFC) tag. In some embodiments, the passive tag 105 may comprise a short range radio tag. The passive tag 105 may be scanned by the wireless scanner 106 of the gas detector device 102. The wireless scanner 106 may forward information received from the passive tag 105 to the processor 114, wherein the processor 114 may store the location information from the passive tag 105 in the memory 116, and wherein the processor 114 may associate new information received from the sensors 103 with the updated location information.

As shown in FIG. 1B, the location indicator 104 may comprise a poster, wherein the passive tag 105 is installed in the poster, making it easy for the user to notice. When the user enters a key location, they may see the poster (e.g. the location indicator 104) and scan their detector against the poster to "check in" to that location.

Figure 2:
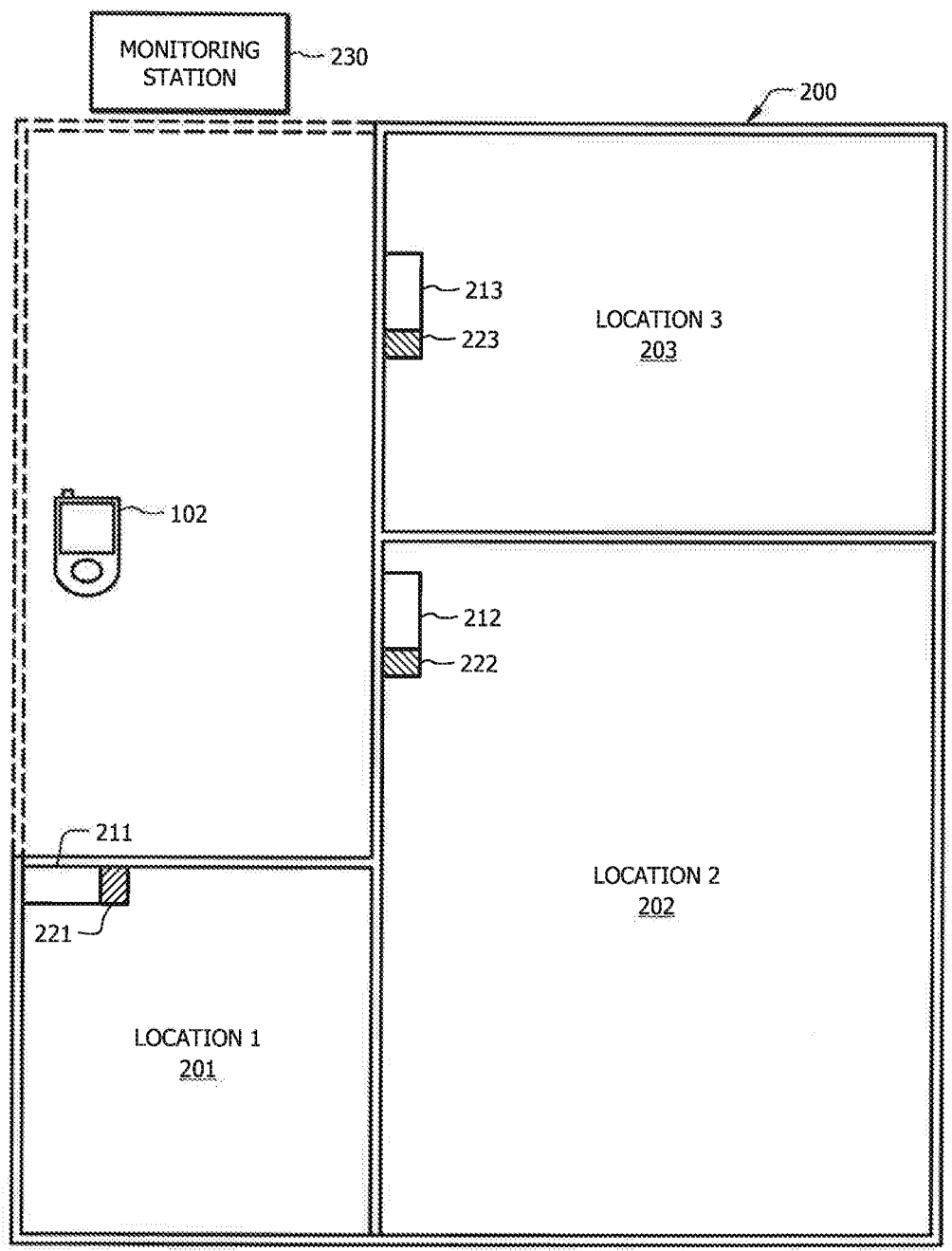
FIG. 2 illustrates a facility map according to an embodiment of the disclosure.

Referring now to FIG. 2, a facility 200 is shown comprising multiple locations or zones. The locations may comprise one or more critical areas, such as entrances or exits. For example, a first location 201 may comprise an entrance 211, a second location 202 may comprise an entrance 212, and a third location 203 may comprise an entrance 213. In some embodiments, the facility 200 may comprise location indicators 221, 222, and 223 located at or near one or more of the entrances 211, 212, 213. The location indicators 221, 222, and 223 may be similar to the location indicator 104 described in FIG. 1, wherein the location indicators may comprise passive tags operable to communicate information about the location(s) when scanned by a gas detector device 102.

In some embodiments, the gas detector device 102 may travel, with a user, between the different locations. When the user enters a new location 201, a user may scan the passive tag of the location indicator 221 with the gas detector device 102 to receive location information at the entrance 211 of the location 201. Then, the gas detector device 102 may update the location information stored by the gas detector device 102, wherein all subsequent readings taken by the (sensors of the) gas detector device 102 may be associated with the updated location information. Similarly, if the gas detector device 102 travels with the user to other locations 202 or 203, the gas detector device 102 may receive new location information by scanning the passive tags at the location indicators 222 and 223, and may update the location information stored on the gas detector device 102 accordingly. In some embodiments, the gas detector device 102 may indicate to a user that a location update is requested or received, and a user may be required to input a confirmation for the update to proceed.

In some embodiments, the gas detector device 102 may also communicate the received location information to a remote monitoring station 230. The remote monitoring station 230 may be monitored by a supervisor, for example. In other embodiments, the location information may be stored locally on the gas detector device 102 and may be accessed later by a monitor or monitoring station.

Figure 3:
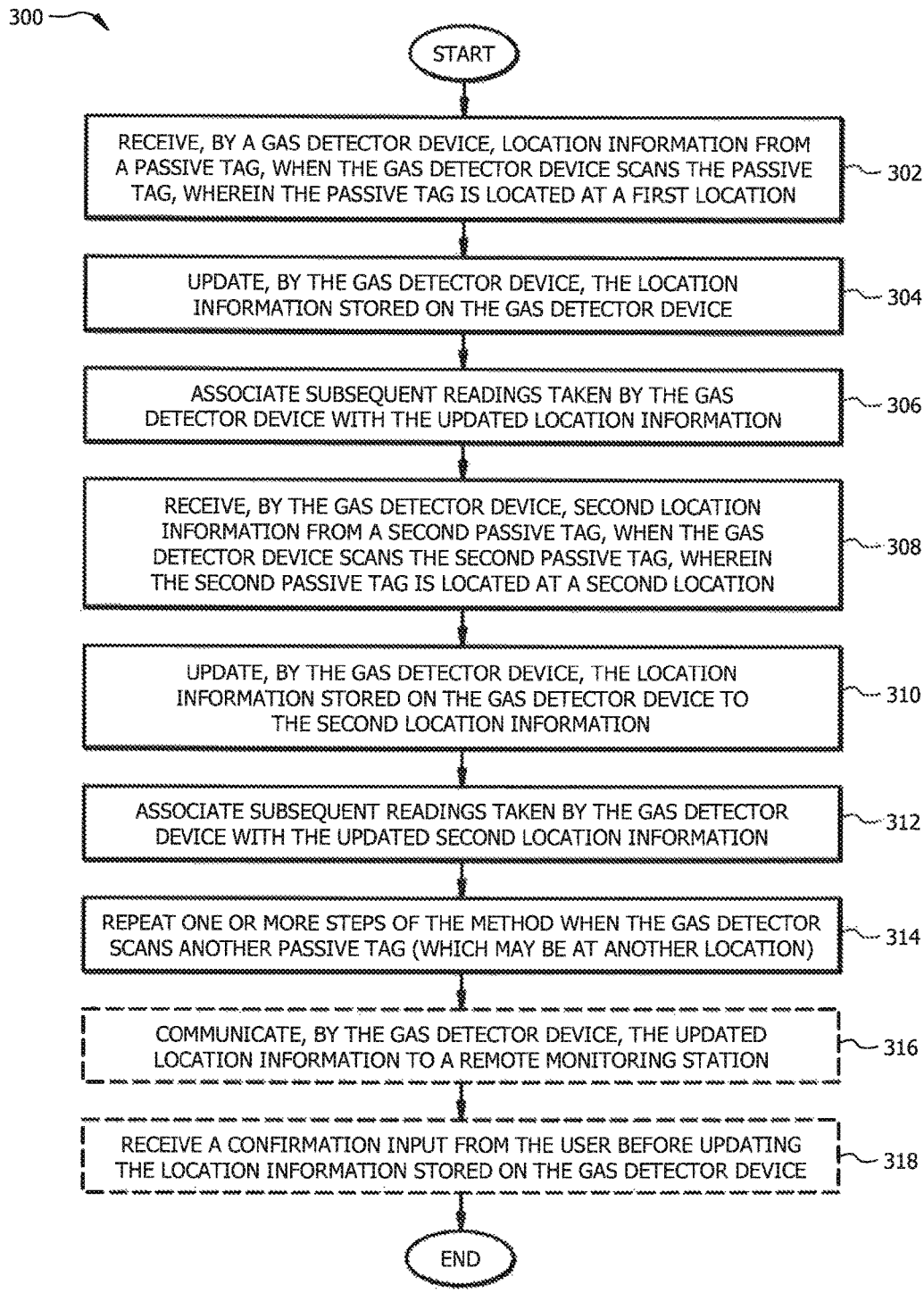
FIG. 3 illustrates a method according to an embodiment of the disclosure.

FIG. 3 illustrates a method for updating the location information on a gas detector device, hi some embodiments, one or more steps of the method 300 may occur in different orders than shown in FIG. 3. At step 302, the gas detector device 102 may receive location information from a passive tag, when the gas detector device scans the passive tag, wherein the passive tag is located at a first location. At step 304, the gas detector device may update the location information stored on the gas detector device using the location information from the passive tag. At step 306, the gas detector device may associate subsequent readings taken by one or more sensors of the gas detector device with the updated location information.

In some embodiments, the gas detector device may scan more than one passive tag, wherein the passive tags may be located at different areas within a facility. At step 308, the gas detector may receive second location information from a second passive tag, when the gas detector device scans the second passive tag, wherein the second passive tag is located at a second location. At step 310, the gas detector device may update the location information stored on the gas detector device using the second location information from the second passive tag. At step 312, the gas detector device may associate subsequent readings taken by one or more sensors of the gas detector device with the updated second location information.

In some embodiments, at step 314, one or more steps of the method may be repeated when the gas detector device scans another passive tag (wherein the passive tags) may be located at different areas within the facility). Optionally, at step 316, the gas detector device may communicate the updated location information to a remote monitoring station. In some embodiments, step 316 may occur after step 304 and/or after step 310. Optionally, at step 318, the gas detector device may receive a confirmation input from the user before updating the location information stored on the gas detector device. In some embodiments, step 318 may occur before step 304 and/or before step 310.

In some embodiments, the passive tag may be located at one or more critical areas of a facility. In some embodiments, the passive tag may be located at one or more entrances to locations within a facility. In some embodiments, the gas detector may scan the passive tag and receive the location information via a wireless scanner incorporated into the gas detector device. In some embodiments, updating the location information stored on the gas detector device occurs automatically.

Some embodiments of the disclosure may comprise a gas detector device comprising one or more sensors operable to detect gases in the air around the gas detector device; a wireless scanner operable to scan one or more passive tags; a memory; and a processor operable to receive and store readings from the one or more sensors of the gas detector; receive location information from the passive tags; update the location information stored in the memory of the gas detector device using the received location information; and associate subsequent readings from the one or more sensors with the updated location information.

In some embodiments, the processor may be further operable to receive second location information from a second passive tag; update the location information stored in the memory of the gas detector device using the received second location information; and associate subsequent readings from the one or more sensors with the updated second location information. In some embodiments, the one or more passive tags are located at critical areas of a facility. In some embodiments, the one or more passive tags are located at one or more entrances to locations within a facility. In some embodiments, the one or more passive tags are incorporated into location indicators. In some embodiments, the location indicators comprise a sigh or notification for the user that they are entering a new location, and therefore should scan the passive tag with their gas detector device. In some embodiments, the gas detector device may further comprise a wireless transmitter, wherein the processor is further operable to communicate the updated location information to a remote monitoring station. In some embodiments, updating the location information occurs automatically. In some embodiments, the processor may be further operable to present a confirmation message to the user via a user interface of the gas detector device; and receive a confirmation input from the user before updating the location information stored on the gas detector device.

Some embodiments of the disclosure may comprise a method for updating the location information on a gas detector device, the method comprising receiving, by a wireless scanner of a gas detector device, location information from a passive tag, when the gas detector device scans the passive tag, wherein the passive tag is located at a first location; updating, by a processor of the gas detector device, the location information stored on the gas detector device using the location information from the passive tag; and associating, by the processor of the gas detector device, subsequent readings taken by one or more sensors of the gas detector device with the updated location information.

In some embodiments, the method may further comprise receiving, by the wireless scanner of the gas detector device, location information from a second passive tag, when the gas detector device scans the second passive tag, wherein the second passive tag is located at a second location; updating, by the processor of the gas detector device, the location information stored on the gas detector device using the second location information from the second passive tag; and associating, by the processor of the gas detector device, subsequent readings taken by the one or more sensors of the gas detector device with the updated second location information.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for updating location information on a gas detector device, the gas detector device comprising a gas sensor, a wireless scanner, a memory, and a processor, the method comprising:
   scanning, by the wireless scanner, a passive tag associated with a first location;
   receiving, by the wireless scanner, location information from the passive tag upon scanning the passive tag;
   updating, by the processor, a location field stored in the memory of the gas detector device to indicate that the gas detector device is present at the first location, based on the location information from the passive tag; and subsequent to updating the location field to indicate that the gas detector device is present at the first location, receiving, by the processor, a first reading from the gas sensor; and associating, by the processor, the first reading with the first location.

2. The method of claim 1, further comprising:

scanning, by the wireless scanner, a second passive tag associated with a second location;

receiving, by the wireless scanner, second location information from the second passive tag upon scanning the second passive tag;

updating, by the processor, the location field to indicate that the gas detector is present at the second location, based on the second location information from the second passive tag; and subsequent to updating the location field to indicate that the gas detector device is present at the second location, receiving, by the processor, a second reading from the gas sensor; and associating, by the processor, the second reading with the second location.

3. The method of claim 1, further comprising repeating one or more steps of the method when the gas detector device scans another passive tag.

4. The method of claim 1, further comprising communicating, by the gas detector device, updated location information to a remote monitoring station.

5. The method of claim 1, wherein the passive tag is located at one or more critical areas of a facility.

6. The method of claim 1, wherein the passive tag is located at one or more entrances to locations within a facility.

7. The method of claim 1, wherein updating the location field occurs automatically upon receiving location information.

8. The method of claim 1, further comprising receiving a confirmation input from a user before updating the location field.

9. A gas detector device comprising:

a gas sensor configured to detect gases in the air around the gas detector device;

a wireless scanner configured to scan a plurality of passive tags associated with a plurality of locations, respectively;

a memory; and a processor operable to:

cause the wireless scanner to scan a first passive tag associated with a first location;

receive first location information from the first passive tag;

update a location field stored in the memory of the gas detector device to indicate that the gas detector device is present at the first location, based on the first location information; and subsequent to updating the location field to indicate that the gas detector device is present at the first location, receive a first reading from the gas sensor; and associate the first reading with the first location.

10. The gas detector device of claim 9, wherein the processor is further operable to:

cause the wireless scanner to scan a second passive tag associated with a second location;

receive second location information from the second passive tag;

update the location field to indicate that the gas detector is present at the second location, based on the second location information; and subsequent to updating the location field to indicate that the gas detector device is present at the second location, receive a second reading from the gas sensor; and associate the subsequent readings from the one or more sensors with the updated second location information.

11. The gas detector device of claim 9, wherein the one or more passive tags are located at critical areas of a facility.

12. The gas detector device of claim 9, wherein the one or more passive tags are located at one or more entrances to locations within a facility.

13. The gas detector device of claim 9, wherein the one or more passive tags are incorporated into location indicators.

14. The gas detector device of claim 13, wherein the location indicators comprise a sign or notification for a user that they are entering a new location, and therefore should scan the passive tag with their gas detector device.

15. The gas detector device of claim 9, further comprising a wireless transmitter, wherein the processor is further operable to communicate the updated location information to a remote monitoring station.

16. The gas detector device of claim 9, wherein updating the location field occurs automatically upon receiving location information.

17. The gas detector device of claim 9, wherein the processor is further operable to:

present a confirmation message to a user via a user interface of the gas detector device; and receive a confirmation input from the user before updating the location field.

18. A method for updating location information on a gas detector device, the gas detector device comprising a gas sensor, a wireless scanner, a memory, and a processor, the method comprising:

scanning, by the wireless scanner, a first passive tag at an entrance to a first facility;

receiving, by the wireless scanner, location information from the first passive tag upon scanning, the first passive tag;

updating, by the processor, a location field stored in the memory of the gas detector device to indicate that the gas detector device is present at the first facility, based on using the location information from the first passive tag; and subsequent to updating the location field to indicate that the gas detector device is present at the first facility, receiving, by the processor, a first reading from the gas sensor; and associating, by the processor, subsequent readings taken by the gas sensor with the first facility.

19. The method of claim 18, further comprising: scanning, by the wireless scanner, a second passive tag associated with an entrance to a second facility;

receiving, by the wireless scanner, location information from the second passive tag upon scanning the second passive tag;

updating, by the processor, the location field to indicate that the gas detector is present at the second facility, based on the second location information from the second passive tag; and subsequent to updating the location field to indicate that the gas detector device is present at the second facility, receiving, by the processor, a second reading from the gas sensor; and associating, by the processor, the second reading with the second facility.

\* \* \* \* \*

UNITED STATES PATENT AND TRADEMARK OFFICE
CERTIFICATE OF CORRECTION

PATENT NO. : 10,088,550 B2  
APPLICATION NO. : 15/045573  
DATED : October 2, 2018  
INVENTOR(S) : Kirk William Johnson, Mahdi Javer and Stephen Mroszczak Page 1 of 1

It is certified that error appears in the above-identified patent and that said Letters Patent is hereby corrected as shown below:

In the Specification

Column 4/Line 2: "device, hi" should be "device. In"

In the Claims

Column 7/Line 49: "to;" should be "to:"

Signed and Sealed this  
Nineteenth Day of March, 2019

Andrei Iancu  
*Director of the United States Patent and Trademark Office*